US010127829B1

(12) United States Patent
Maly et al.

(10) Patent No.: US 10,127,829 B1
(45) Date of Patent: Nov. 13, 2018

(54) METHOD AND SYSTEM FOR CALCULATING PROBABILITIES OF CAUSATION OF SPECIFIED HEALTH CONDITIONS BY FOODS

(71) Applicants: Michael Paul Maly, Cleveland, OH (US); Yulia Maly, Cleveland, OH (US)

(72) Inventors: Michael Paul Maly, Cleveland, OH (US); Yulia Maly, Cleveland, OH (US)

(*) Notice: Subject to any disclaimer, the term of this patent is extended or adjusted under 35 U.S.C. 154(b) by 162 days.

(21) Appl. No.: 15/159,250

(22) Filed: May 19, 2016

Related U.S. Application Data

(60) Provisional application No. 62/165,518, filed on May 22, 2015.

(51) Int. Cl.
A63F 9/24 (2006.01)
G09B 19/00 (2006.01)
A61B 5/00 (2006.01)
G09B 5/12 (2006.01)

(52) U.S. Cl.
CPC ........ G09B 19/0092 (2013.01); A61B 5/4866 (2013.01); A61B 5/7275 (2013.01); G09B 5/125 (2013.01)

(58) Field of Classification Search
CPC .. G09B 19/0092; A61B 5/4866; A61B 5/7275
See application file for complete search history.

(56) References Cited

U.S. PATENT DOCUMENTS

| 6,179,778 | B1 | 1/2001 | Leonov et al. | |
|---|---|---|---|---|
| 7,613,619 | B1* | 11/2009 | Harter | A61B 5/00 705/2 |
| 7,908,181 | B2 | 3/2011 | Dotson | |
| 2004/0107116 | A1 | 6/2004 | Brown | |
| 2004/0176666 | A1 | 9/2004 | Chait | |
| 2004/0225529 | A1* | 11/2004 | Snyder | G06F 19/3456 705/2 |
| 2005/0236004 | A1* | 10/2005 | Magnuson | G06Q 50/24 128/898 |
| 2005/0240444 | A1* | 10/2005 | Wooten | G06F 19/3481 705/3 |
| 2007/0118398 | A1* | 5/2007 | Perls | G06F 19/328 705/2 |

(Continued)

Primary Examiner — Steve Rowland
(74) Attorney, Agent, or Firm — Tarolli, Sundheim, Covell & Tummino LLP

(57) ABSTRACT

A method includes the steps of receiving data indicative of a selected health condition; identifying one or more trigger substances associated with the selected health condition; identifying one or more foods containing the identified one or more trigger substances, including the concentration of the trigger substance; receiving data indicative of a selection of the one or more identified foods, including the amount of the food consumed within a specified time interval; identifying one or more risk factors associated with the one or more trigger substances contained in the selected one or more foods; receiving data indicative of a selection of the one or more identified risk factors; and calculating a probability of causation of the selected health condition based on the selected foods, weight values associated with the identified trigger factors contained in the selected foods indicative of the relative significance of the substance as a trigger of the selected health condition, and the selected risk factors.

20 Claims, 5 Drawing Sheets

(56) References Cited

U.S. PATENT DOCUMENTS

| | | |
|---|---|---|
| 2008/0069929 A1 | 3/2008 | Labouze |
| 2008/0108881 A1* | 5/2008 | Stupp ................. G06F 17/18 600/300 |
| 2012/0265650 A1 | 10/2012 | Gusich |
| 2013/0108993 A1 | 5/2013 | Katz |
| 2013/0157232 A1* | 6/2013 | Ehrenkranz ........ G01G 19/4146 434/127 |
| 2016/0128618 A1* | 5/2016 | Lee ..................... A61B 5/16 600/595 |

* cited by examiner

300

**Your condition: *Migraine***

| *Trigger Food* | *Causation Probability* | *Trigger Substance* |
|---|---|---|
| Cheese, Cheddar | 42% | Tyramine |
| Chicken Liver | 23% | Tyramine |
| Beer, Tap | 18% | Tyramine |
| Bananas | 11% | Tyramine |
| Red Wine (Chianti) | 6% | Tyramine |

*Contributing Risk Factors:*
- ✓ Age
- ✓ Gender
- ✓ Medication
- ✓ Smoking

FIG. 3

METHOD AND SYSTEM FOR CALCULATING PROBABILITIES OF CAUSATION OF SPECIFIED HEALTH CONDITIONS BY FOODS

CROSS-REFERENCE TO RELATED APPLICATION

This application claims priority from U.S. Patent Application No. 62/165,518 filed on May 22, 2015, which is incorporated by reference herein in its entirety.

FIELD OF DISCLOSURE

The present disclosure relates to the field of medical diagnostics and nutrition, in particular to identifying and quantifying a causal relationship between certain health conditions and foods consumed by the affected individuals.

BACKGROUND

Physicians and scientists have long been aware that certain chemical substances contained in foods have an adverse effect on the human body. The list of health disorders linked to foods we eat is vast, including, among many others: hypertension, heart disease, obesity, gastrointestinal problems (Celiac, IBS, chronic constipation, bloating), diabetes, chronic fatigue, skin disorders, arthritis, autoimmune disorders, ADD and migraines. Although some diseases are very complex in nature and take many months or years to develop, others have a more defined and immediate connection to foods we eat daily.

Both consumers and healthcare practitioners have become increasingly aware of the impact foods have on our health. Substantial resources have been invested into identifying foods linked to most common health disorders (hereinafter referred to as "Trigger Foods").

An example of Trigger Foods is those foods containing Gluten. Research increasingly is backing up claims that millions of people are sensitive to this protein compound found in wheat. Emerging studies have shown gluten-free diets to be helpful for reducing symptoms associated with a wide variety of serious health disorders, such as ADD/ADHD, autism, depression, chronic fatigue, Irritable Bowel Syndrome and general digestive health.

Other notable Trigger Foods include, by way of example, cow milk, cane sugar, eggs, and nightshade vegetables. The chemical substances contained in foods that cause the adverse effect on the body (herein referred to as "Trigger Substances") include, among others, certain proteins (such as gluten, casein, lectin), sugars (lactose), alkaloids, and biogenic amines (histamine, Tyramine).

Physicians and nutritionists, in the course of their practice, routinely attempt to identify the link between Trigger Foods, Trigger Substances and certain health conditions in their patients. This is typically done through a process of elimination. Elimination diets have become a staple in the arsenal of treatment modalities of healthcare practitioners. Unfortunately, identifying the Trigger Foods through elimination diets is a daunting hit-and-miss process that takes months to complete. Patients are required to maintain detailed food journals in the hope of identifying a single Trigger Food for their health condition. Complicating matters is that many health conditions can be caused by multiple Trigger Substances, some Trigger Substances can cause multiple health conditions, and some Trigger Foods contain multiple Trigger Substances. Thus, if a patient presents with multiple symptoms, it becomes extremely difficult, if not impossible, to identify the correct Trigger Foods responsible for the patient's health conditions via a manual process due to the large number of possible combinations of Trigger Foods and Trigger Substances. Furthermore, the effect of Trigger Substances on the body is dose dependent; i.e., a higher amount of a Trigger Substance contained in a Trigger Food will have a more pronounced adverse effect. Thus, it is not enough to merely identify a specific Trigger Food that may contribute to a health condition; it is necessary to know how much relevant Trigger Substance is actually contained in the specific Trigger Food.

Moreover, the practitioner has to consider additional variables affecting the individual patient's susceptibility to Trigger Substances; these may include age, gender, ethnicity, genetic predisposition, medications taken, and medical history, among others. Even if one could correctly identify and separate all Trigger Foods and Trigger Substances responsible for the individual's symptoms via a manual process, it may be difficult and time-consuming and may not be feasible to quantify the effect of those Trigger Foods and rank them in the order of significance for each symptom (i.e., rank from highest to lowest the probability of causation of a particular symptom by each Trigger Food).

Thus, a method or system of efficiently and systematically identifying and quantifying the causation probability of certain health conditions by specific Trigger Substances and Trigger Foods consumed by the individual may be beneficial. Such a method or system would be of significant benefit in modalities of disease prevention and treatment, and could be incorporated into standard differential diagnosis methodology universally used by healthcare practitioners throughout the world.

SUMMARY

In one embodiment, a system for calculating probabilities of causation of specified health conditions includes one or more processors, one or more computer-readable tangible storage devices, and program instructions stored on at least one of the one or more storage devices for execution by at least one of the one or more processors. The program instructions include: first program instructions to receive data indicative of a selected health condition; second program instructions to identify one or more trigger substances associated with the selected health condition; third program instructions to identify one or more foods containing the identified one or more Trigger Substances, including the concentration of the Trigger Substance; fourth program instructions to receive data indicative of a selection of the one or more identified foods, including the amount of the food consumed within a specified time interval; fifth program instructions identify one or more risk factors associated with the one or more Trigger Substances contained in the selected one or more foods; sixth program instructions to receive data indicative of a selection of the one or more identified risk factors; and seventh program instructions to calculate a probability of causation of the selected health condition based on the selected foods, weight values associated with the identified Trigger Substances contained in the selected foods indicative of the relative significance of the substance as a trigger of the selected health condition, and the selected risk factors.

In one example embodiment, a method for calculating probabilities of causation of specified health conditions includes the steps of receiving data indicative of a selected health condition; identifying one or more Trigger Substances associated with the selected health condition; identifying one or more foods containing the identified one or more Trigger Substances, including the concentration of the Trigger Substance; receiving data indicative of a selection of the one or more identified foods, including the amount of the food consumed within a specified time interval; identifying one or more risk factors associated with the selected one or more foods; receiving data indicative of a selection of the one or more identified risk factors; and calculating a probability of causation of the selected health condition based on the selected foods, weight values associated with the identified trigger factors contained in the selected foods indicative of the relative significance of the substance as a trigger of the selected health condition, and the selected risk factors.

In one example embodiment, a computer program product includes one or more computer-readable tangible storage devices, and program instructions stored on at least one of the one or more storage devices. The program instructions include; first program instructions to receive data indicative of a selected health condition: second program instructions to identify one or more Trigger Substances associated with the selected health condition; third program instructions to identify one or more foods containing the identified one or more Trigger Substances, including the concentration of the Trigger Substance; fourth program instructions to receive data indicative of a selection of the one or more identified foods, including the amount of the food consumed within a specified time interval; fifth program instructions identify one or more risk factors associated with the one or more Trigger Substances contained in the selected one or more foods; sixth program instructions to receive data indicative of a selection of the one or more identified risk factors; and seventh program instructions to calculate a probability of causation of the selected health condition based on the selected foods, weight values associated with the identified Trigger Substances contained in the selected foods indicative of the relative significance of the substance as a trigger of the selected health condition, and the selected risk factors.

BRIEF DESCRIPTION OF THE DRAWINGS

In the accompanying drawings, structures are illustrated that, together with the detailed description provided below, describe exemplary embodiments of the claimed invention. Like elements are identified with the same reference numerals. It should be understood that elements shown as a single component may be replaced with multiple components, and elements shown as multiple components may be replaced with a single component. The drawings are not to scale and the proportion of certain elements may be exaggerated for the purpose of illustration.

FIG. 3 illustrates an example display of causal relations between trigger foods, Trigger Substances and health conditions.

DETAILED DESCRIPTION

Figure 1:
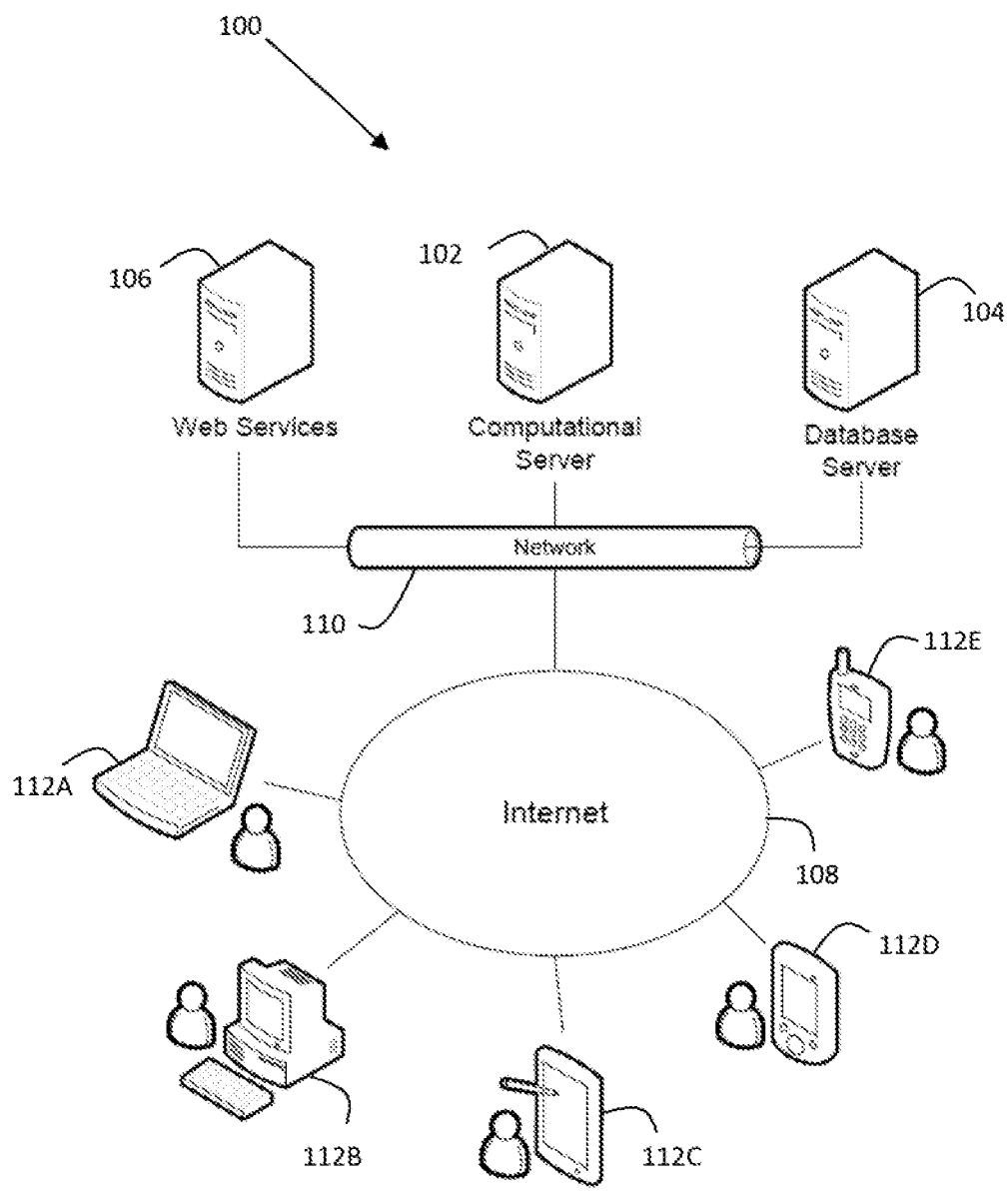
FIG. 1 illustrates an example system for calculating probabilities of causation of specified health conditions.

FIG. 1 illustrates an example system 100 for calculating probabilities of causation of specified health conditions. The system includes a computational server 102 configured to identify possible Trigger Substances that may cause a specified health condition in an individual, identify possible Trigger Foods, consumed by an individual during a defined time interval that may cause a specified health condition in that individual and calculate numeric probability of causation of the specified health conditions by each of the aforementioned Trigger Foods. The computational server 102 also displays or communicates the results of the foregoing calculations for each specified health condition, including the list of Trigger Foods, causation probability by each Trigger Food (either in % or another numeric scale), Trigger Substance(s) within each Trigger Food, and relevant contributing risk factors (i.e., gender, age, ethnicity, medical condition, medications, etc).

The system 100 further includes a database server 104 including one or more databases for storing information accessible by the computational server 102. The computational server 102 is configured to access the information stored by the database server 104 in order to access relevant information needed to perform the probability calculations. Example databases stored by the database server 104 may include health conditions attributable to specific Trigger Foods, Trigger Substances known to cause specific Health Conditions, Trigger Foods containing Trigger Substances (including relative concentration), Risk Factors for each Health Condition associated with Trigger Substances, and User Data including data received from a user. It should be appreciated that database server 104 may include additional suitable database.

A web services computer 106 is configured to provide a web portal and user interface for accessing and interacting with the computational server 102. The web services computer 106 is accessible over the Internet 108 via network 110 by one or more user computing devices 112A-112E (hereinafter referred to as "user device 112"). The user device 112 is configured to interact with the web services computer 106 and with the computational server 102. In particular, the user device 112 is configured to receive input from a user and communicate the input to computational server 102. The user device 112 is further configured to receive data from the computational server 102 and communicate information to the user. The user device 112 may include any suitable computing device such as, for example, a laptop computer 112A, a desktop computer 112B, a tablet computer 112C, a personal digital assistant 112D, or smartphone 112E.

It should be appreciated that the calculations and analysis performed by the computational server 102 is rooted in cause-and-effect connections between chemical substances contained in certain foods and human body's response to those substances commonly understood by one skilled in the art, as are the specific physiological pathways and mechanisms of the body's response to the aforementioned chemical substances.

By way of example, Tyramine, a biogenic amine compound derived from amino acid Tyrosine, is a known migraine trigger in certain individuals. Tyramine is widely found in foods consumed by many individuals. Concentration of Tyramine in foods varies significantly, based not only on the food in question but also on the condition of the food (i.e., ripe banana has a higher content of Tyramine than green banana, etc.). In the human body, Tyramine releases catecholamines epinephrine, norepinephrine and dopamine. Ingestion of foods rich in Tyramine, coupled with reduced activity of an enzyme responsible for breaking it down, Monoamine Oxidase (MAO), can trigger vasoactive response leading to migraines, cluster headaches and even hypertensive crisis.

In particular, the computational server 102 calculates probability of causation of a health condition (such as migraine, for example) in an individual by specific Trigger Foods as a function of (i) the amount of each Trigger Food containing a Trigger Substance known to cause the health condition in question (such as Tyramine, for example) consumed by the individual within a specified time interval; (ii) the concentration of the Trigger Substance in each Trigger Food consumed within a specified time interval; (iii) the relevant Risk Factors in the individual associated with Tyramine; and (iv) the number of concurrent Health Conditions, experienced by the individual, that may be caused by the Trigger Substance.

It should be appreciated that the actual concentration of a specific Trigger Substance in a Trigger Food may be predefined and retrieved from database server 104. Actual concentration of a Trigger Substance in a Trigger Food may be, for example, 42 mg of Tyramine per 1 oz Cheddar Cheese, 1.6 mg of Tyramine per 1 oz of Gorgonzola Cheese, 25.4 mg Tyramine per 1 L of Chianti Wine, and so on.

In the event that actual concentration of a specific Trigger Substance in a Trigger Food is not available in the database server 104, relative concentration is assigned using a numeric unit scale (such as 1-5, with 1 being the lowest and 5 being the highest, for example). Relative concentrations of a Trigger Substance in a Trigger Food may be, for example, 5 units of Casein per 1 oz of Cow Cheese, 3 units of Casein per 1 oz of Goat Cheese, 1 unit of Casein per 1 oz of Margarine, and so on. It should be appreciated that relative concentrations of Trigger Substances in Trigger Foods are available in existing scientific references.

Risk Factors associated with Tyramine, for example, are those factors affecting MAO activity in the body. These include, among others, elevated estrogen levels, tobacco use, and MAO inhibitor medications. Furthermore, consumption of alcohol accelerates absorption of Tyramine into the bloodstream, amplifying the effect of Tyramine-containing Trigger Foods. Based on the foregoing, therefore, Risk Factors for Tyramine induced migraine headaches would include age, gender, obesity, other health conditions affecting estrogen production, tobacco use, and alcohol use, for example.

Concurrent multiple health conditions in an individual attributable to a specific Trigger Substance are indicative of that individual's increased sensitivity to the substance. Consequently, the higher the number of such concurrent health conditions, the greater the probability that each such condition is caused by the specific Trigger Substance.

It should be appreciated that causal relationships analogous to the above exist for many other Trigger Substances and corresponding health conditions. By way of example, such additional documented causal relationships include Gluten to Irritable Bowel Syndrome, Lactose to abdominal discomfort, Alkaloids to Arthritis and joint pain, Casein to Gastrointestinal disorders, Casein to sinuses and ear infections, Lectin to acne and other skin disorders, etc. Although not individually described herein, it should be appreciated that the computation server 102 may be used to calculate the probability of any suitable causation of the health disorders by relevant Trigger Substances. Thus, the computation server 102 may be applied to and incorporate all suitable relationships between Trigger Substances and related health conditions.

Figure 2:
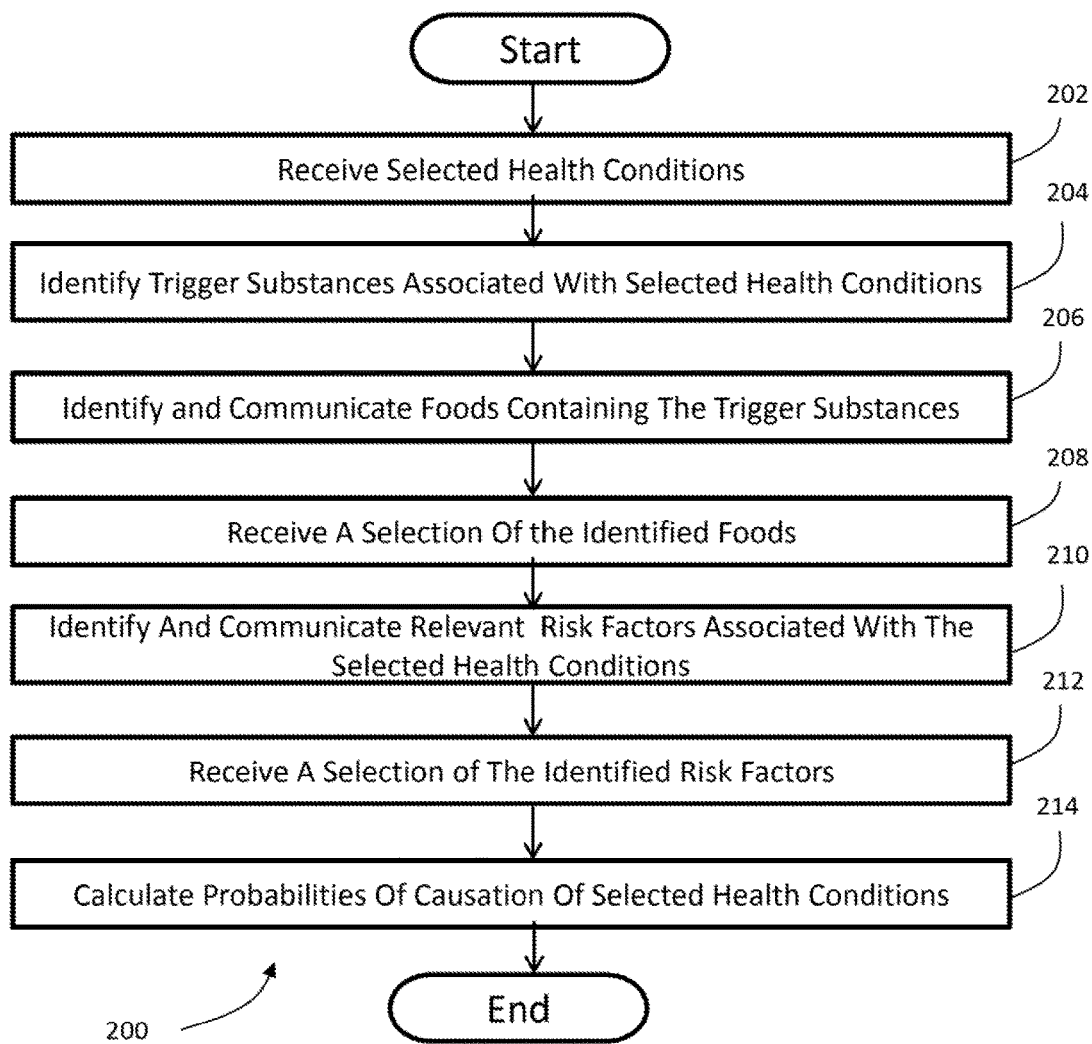
FIG. 2 illustrates an example method for calculating probabilities of causation of specified health conditions.

The computation server 102 will be further understood and appreciated as the method 200 illustrated in FIG. 2 is described herein. At step 202, the computation server 102 receives a selection of one or more Health Conditions. The selections can be received from a user via a user device 112, for example. In one example, the computation server 102 communicates Health Conditions to the user device 112 for selection. Additionally, the computation server 102 may retrieve a list of Health Conditions from database server 104.

At step 202, the computation server 102 identifies one or more Trigger Substances associated with the received selected Health Conditions. In one example, the computation server 102 identifies the one or more Trigger Substances by cross-referencing a Trigger Substances database provided by database server 104 with the received, selected Health Conditions.

At step 206, the computation server 102 identifies one or more foods containing the identified Trigger Substances. In one example, the computation server 102 identifies the one or more foods by cross-referencing a Foods database provided by database server 104 with the identified Trigger Substances. Thus, the identified one or more foods are filtered based on the identified Trigger Substances attributable to the received selected Health Condition. The computation server 102 further communicates the identified one or more foods to the user device 112 for display to a user. The one or more foods may be displayed by the user device in any suitable format, such as by food group or alphabetically, for example.

At step 208, the computation server 102 receives a selection of the identified foods. In one example, the selection—representation of foods consumed by a user is received from the user device 112 associated with the user. In one example, the computation server 102 also receives data indicative of the frequency of consumption of the selection of identified foods in given intervals. For example, the received data may indicate that the user consumes a selected food, once a month, once a week, daily, and so on.

At step 210, the computation server 102 identifies relevant risk factors associated with received Health Conditions. In one example, the computation server 102 identifies the relevant Risk Factors by cross-referencing a Risk Factors database provided by database server 104 with the received selected Health Conditions. Relevant risk factors may include, for example, medications, specific health history items, gender, age, and so on. The computation server 102 further communicates the identified risk factors to the user device 112 for displaying to the user.

It should be appreciated that, although various references are made herein to the computation server 102 retrieving and identifying various information from databases provided by database server 104, the computation server 102 may also retrieve and identify such data using other suitable methods from other suitable data sources or providers.

At step 212, the computation server 102 receives a selection of the identified risk factors. For example, a user may select, via the user device 112, specific medications currently being consumed, specific health conditions experienced, and so on, which are then communicated to the computation server 102.

At step 214, the computation server 102 calculates the probabilities of causation of the selected Health Conditions by the selected Trigger Foods. In particular, the computation server 102 calculates the probabilities based on the amount of each Trigger Food consumed within a specified time interval, the actual or relative concentration of each identified Trigger Substance in each identified Trigger Food, relevant identified Risk Factors associated with each identified Trigger Substance, and the number of concurrent Health Conditions experienced by the user, caused by specific Trigger Substances.

Accordingly, the calculation can be described as:

$$P(x)=f[AMT(x),C(y)_x,RF(r)_y,N_y] \quad \text{Equ(1)}$$

where: P(x) is the probability of causation of Health Condition by food(x); AMT(x) is the amount of food(x) consumed by the individual within a specified time interval; $C(y)_x$ is the concentration of Trigger Substance(y) in food (x); $RF(r)_y$ is risk Factors (r) for Health Conditions associated with Trigger Substance(y); and $N_y$ is the number of concurrent Health Conditions, experienced by the user, caused by Trigger Substance (y).

Once the probabilities are calculated, the computation server 102 communicates the results to the user device 112 for display to a user. In one example, the computation server 102 generates a summary report and communicates to the user device 112, the report including specified Health Condition(s), all identified Trigger Foods consumed by the User associated with the specified Health Condition(s), Probabilities of causation of the Health Condition(s) by each Trigger Food consumed by the User, Trigger Substance(s) associated with each Trigger Food, and User's Risk Factors affecting probabilities of causation of the Health Condition by each Trigger Food consumed by the User. FIG. 3 illustrates an example display 300 of causal relations between Trigger Foods, Trigger Substances, and health conditions that may be displayed on the user device 112.

In one example, the computational server 102 repeats the calculation step 214 for each Health Condition if multiple Conditions are selected by the User.

To further illustrate the step 214 of the computation server 102 calculating the probabilities, an example of Trigger Foods of migraine headaches is described herein. For illustration purposes, Trigger Substances Tyramine and Potassium Nitrate ($KNO_3$) are known Migraine triggers. The example calculation described herein illustrates probabilities of causation of a Migraine in a User by Trigger Foods containing Tyramine and $KNO_3$.

The probability of causation of a Migraine by food(x), expressed in %, would be calculated as follows:

$$P(x) = \frac{100.0 * ([AMT(x)*C(T)_x * W_T] + [AMT(x)*C(N)_x * W_N])}{(TS_T * W_T) + (TS_N * W_N)} \quad \text{Equ (2)}$$

where: P(x) is probability of causation of the Health Condition by food(x); AMT(x) is the amount of food(x) consumed by the individual within a specified time interval; $C(T)_x$ is concentration of Tyramine in food(x); $C(N)_x$ is concentration of $KNO_3$ in food(x); $W_T$ is Weight value assigned to Tyramine reflecting relative significance of Tyramine as a Migraine trigger, $W_N$ is Weight value assigned to $KNO_3$ reflecting relative significance of $KNO_3$ as a Migraine trigger; and $TS_T$ is total amount of Tyramine in all Trigger Foods consumed by the User within a specified time interval, and $TS_N$ is total amount of $KNO_3$ in all Trigger Foods consumed by the User within a specified time interval.

The above calculation is repeated for each Trigger Food containing Tyramine and/or $KNO_3$ consumed by the User within a specified period.

Thus, the general equation for calculating probability of causation of a Health Condition by Trigger Food(x) is:

$$P(x) = \frac{100.0 * \sum_{i=1}^{n} [AMT(x)*C(i)_x * W_i]}{\sum_{i=1}^{n} [TS_i * W_i]} \quad \text{Equ (3)}$$

where: P(x) is probability of causation of the Health Condition by food(x); AMT(x) is amount of food(x) consumed within a specified time interval; $C(i)_x$ is concentration of Trigger Substance(i) in food (x); $W_i$ is Weight value assigned to Trigger Substance(i) reflecting relative significance of the substance as a trigger of the specified Health Condition; n is number of Trigger Substances that can cause the specified Health Condition; and $TS_i$ is total amount of Trigger Substance(i) in all Trigger Foods consumed by the User within a specified time interval. It should be appreciated that weight value $W_i$ reflects a likelihood that a particular Trigger Substance is the true cause of the specified Health Condition as compared to other possible Trigger Substances. Thus, higher values of $W_i$ reflect greater correlation of Trigger Substance(i) to the specified Health Condition. This value is assigned based on experience or available data, for example.

In the event relevant Risk Factors exist for a specified Health Condition, the results of the above calculation are further adjusted for these Risk Factors by applying function $RF(n)_y$. The function $RF(n)_y$ must be defined for each Health Condition and Trigger Substance combination.

By way of example, the probability of causation of Migraine by Tyramine is increased by Risk Factors inhibiting the activity of MAO enzyme. These Risk Factors include: MAO inhibitor medications (such as Zelapar, Marplan, Emsam, etc.); Elevated estrogen levels (due to Gender, Age, certain health conditions); and tobacco use.

The above Risk Factors increase the probability of a Migraine being triggered by foods containing Tyramine by effectively reducing the User's threshold of tolerance to Tyramine. Typical Tyramine tolerance threshold (THtol) in an average person is 1400 mg/week. The effective Tyramine threshold in a person on MOA inhibitor therapy is only 70 mg/week. Elevated estrogen level further decreases the Tyramine threshold by a factor Fest. Tobacco use further decreases the Tyramine threshold by a factor Ftob. Accordingly, the above probability calculations would be modified by adjusting Tyramine's Weight value as a function of THtol, Fest, and Ftob.

Figure 4:
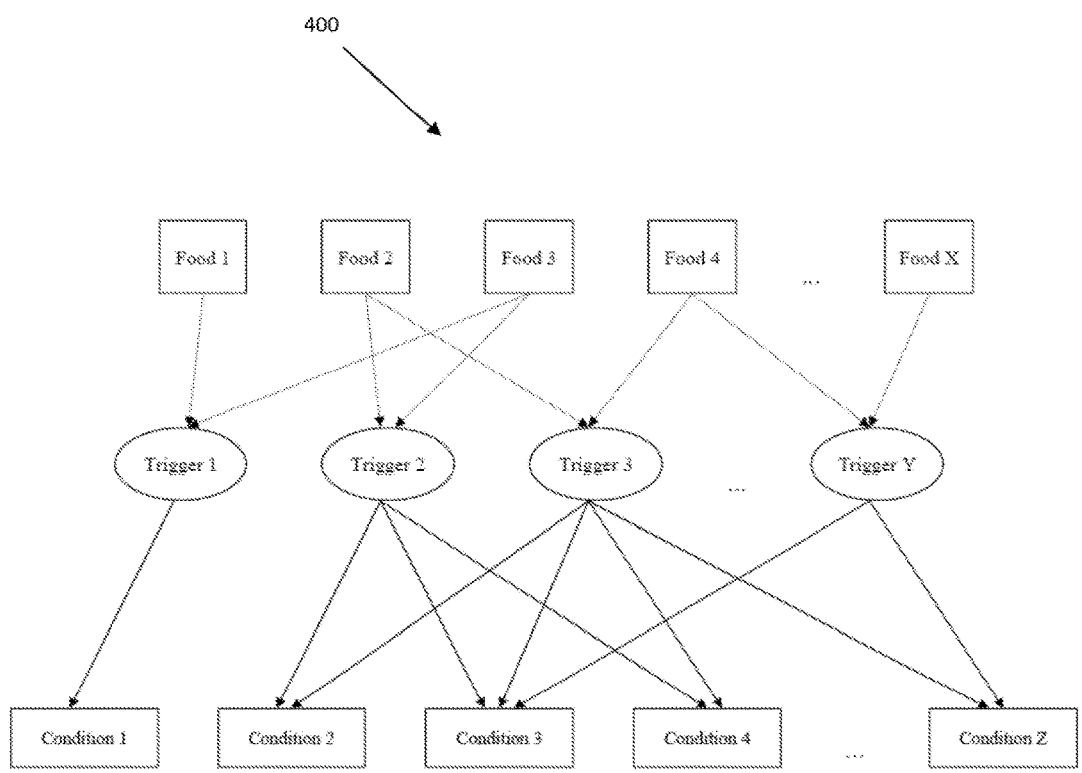
FIG. 4 illustrates an example causal relations diagram.

It should be appreciated that in the event a user specifies concurrent Health Conditions caused by the same Trigger Substance, as illustrated in the causal relations diagram 400 in FIG. 4, the probabilities of causation of each Health Condition by each Trigger Food are modified by adjusting Weight values assigned to each Trigger Substance using known probabilistic methods or Bayesian analysis.

Figure 5:
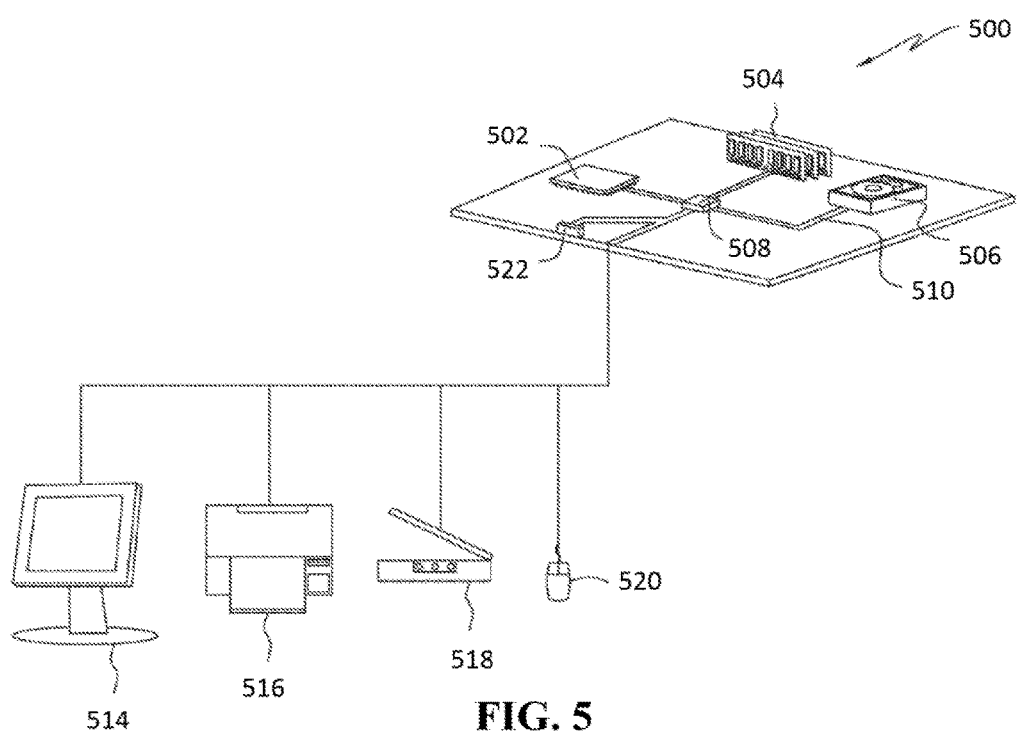
FIG. 5 is a schematic diagram of an example computer for implementing the example computational server of FIG. 1.

FIG. 5 is a schematic diagram of an example computer for implementing the example computational server 102 of FIG. 1. The example computer 500 is intended to represent various forms of digital computers, including laptops, desktops, handheld computers, tablet computers, smartphones, servers, and other similar types of computing devices. Computer 500 includes a processor 502, memory 504, a storage device 506, and a communication port 508, operably connected by an interface 510 via a bus 512.

Processor 502 processes instructions, via memory 504, for execution within computer 800. In an example embodiment, multiple processors along with multiple memories may be used.

Memory 504 may be volatile memory or non-volatile memory. Memory 504 may be a computer-readable medium, such as a magnetic disk or optical disk. Storage device 506 may be a computer-readable medium, such as floppy disk devices, a hard disk device, optical disk device, a tape device, a flash memory, phase change memory, or other similar solid state memory device, or an array of devices, including devices in a storage area network of other configurations. A computer program product can be tangibly embodied in a computer readable medium such as memory 504 or storage device 506.

Computer 500 can be coupled to one or more input and output devices such as a display 514, a printer 516, a scanner 518, and a mouse 520.

While example systems, methods, and so on, have been illustrated by describing examples, and while the examples have been described in considerable detail, it is not the intention to restrict or in any way limit the scope of the appended claims to such detail. It is, of course, not possible to describe every conceivable combination of components or methodologies for purposes of describing the systems, methods, and so on, described herein. Additional advantages and modifications will readily appear to those skilled in the art. Therefore, the invention is not limited to the specific details, and illustrative examples shown or described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995). Also, to the extent that the terms "in" or "into" are used in the specification or the claims, it is intended to additionally mean "on" or "onto." Furthermore, to the extent the term "connect" is used in the specification or claims, it is intended to mean not only "directly connected to," but also "indirectly connected to" such as connected through another component or components.

The invention claimed is:

1. A system for calculating probabilities of causation of specified health conditions, the system comprising one or more processors, one or more computer-readable tangible storage devices, and program instructions stored on at least one of the one or more storage devices for execution by at least one of the one or more processors, the program instructions comprising:
   first program instructions to receive data indicative of a selected health condition;
   second program instructions to identify one or more trigger substances associated with the selected health condition;
   third program instructions to identify one or more foods containing the identified one or more trigger substances, including the concentration of the trigger substance;
   fourth program instructions to receive data indicative of a selection of the one or more identified foods, including the amount of the food consumed within a specified time interval;
   fifth program instructions identify one or more risk factors associated with the one or more trigger substances contained in the selected one or more foods, wherein the one or more risk factor increases the probability of the health condition being triggered by the one or more trigger substances;
   sixth program instructions to receive data indicative of a selection of the one or more identified risk factors; and
   seventh program instructions to calculate a probability of causation of the selected health condition by the selected foods, based on the concentration of the identified trigger substances in the selected foods, weight values associated with the identified trigger substances contained in the selected foods indicative of the relative correlation between the trigger substance and the occurrence of the selected health condition, and the selected risk factors.

2. The system of claim 1, wherein the program instructions further comprise eighth program instructions for communicating data indicative of a summary report, comprising the selected health condition, the one or more identified foods, the calculated probability of causation of the selected health condition, the identified trigger substances associated with the selected foods, and the identified risk factors to a user computing device.

3. The system of claim 2, wherein the system is configured to calculate probabilities for a plurality of selected health conditions and to communicate a plurality of summary reports to the user computing device.

4. The system of claim 1, wherein the second program instructions identifies trigger substances by cross referencing a trigger substances database with the selected health conditions, wherein the third program instructions identifies foods by cross referencing a foods database with the identified trigger substances, and wherein the fifth program instructions identifies risk factors by cross referencing a risk factors database with the selected health conditions.

5. The system of claim 1, wherein the concentration of the trigger substance comprises an actual value.

6. The system of claim 1, wherein the concentration of the trigger substance comprises a relative value.

7. The system of claim 1, wherein the program instructions further comprise ninth program instructions to modify the probabilities of causation of a health condition by a trigger food by adjusting weight values assigned to a trigger substance associated with the trigger food using one of a probabilistic method analysis and Bayesian analysis responsive to the first program instructions receiving data indicative of a plurality of selected health conditions caused by the same trigger substance.

8. A method for calculating probabilities of causation of specified health conditions, comprising the steps of:
   a computer receiving data indicative of a selected health condition;
   a computer identifying one or more trigger substances associated with the selected health condition;
   a computer identifying one or more foods containing the identified one or more trigger substances, including the concentration of the trigger substance;
   a computer receiving data indicative of a selection of the one or more identified foods, including the amount of the food consumed within a specified time interval;

a computer identifying one or more risk factors associated with the selected one or more foods, wherein the one or more risk factor increases the probability of the selected health condition being triggered by the one or more trigger substances;

a computer receiving data indicative of a selection of the one or more identified risk factors;

a computer calculating a probability of causation of the selected health condition by the selected foods, based on the concentration of the identified trigger substances in the selected foods, weight values associated with the identified trigger substances contained in the selected foods indicative of the relative correlation between the trigger substance and the occurrence of the selected health condition, and the selected risk factors.

9. The method of claim 8, further comprising the step of a computer communicating data indicative of a summary report, comprising the selected health condition, the one or more identified foods, the calculated probability of causation of the selected health condition, the identified trigger substances associated with the selected foods, and the identified risk factors to a user computing device.

10. The method of claim 9, further comprising the step of calculating probabilities for a plurality of selected health conditions and communicating a plurality of summary reports to the user computing device.

11. The method of claim 8, further comprising identifying trigger substances by cross referencing a trigger substances database with the selected health conditions, identifying foods by cross referencing a foods database with the identified trigger substances, and identifying risk factors by cross referencing a risk factors database with the selected health conditions.

12. The method of claim 8, wherein the concentration of the trigger substance comprises an actual value.

13. The method of claim 8, wherein the concentration of the trigger substance comprises a relative value.

14. The method of claim 8, further comprising the step of modifying the probabilities of causation of a health condition by a trigger food by adjusting weight values assigned to a trigger substance associated with the trigger food using one of a probabilistic method analysis and Bayesian analysis responsive to the first program instructions receiving data indicative of a plurality of selected health conditions caused by the same trigger substance.

15. A computer program product comprising one or more computer-readable non-transitory tangible storage devices, and program instructions stored on at least one of the one or more storage devices, the program instructions comprising:

first program instructions to receive data indicative of a selected health condition;

second program instructions to identify one or more trigger substances associated with the selected health condition;

third program instructions to identify one or more foods containing the identified one or more trigger substances, including the concentration of the trigger substance;

fourth program instructions to receive data indicative of a selection of the one or more identified foods, including the amount of the food consumed within a specified time interval;

fifth program instructions identify one or more risk factors associated with the one or more trigger substances contained in the selected one or more foods, wherein the one or more risk factor increases the probability of the health condition being triggered by the one or more trigger substances;

sixth program instructions to receive data indicative of a selection of the one or more identified risk factors; and seventh program instructions to calculate a probability of causation of the selected health condition by the selected foods, the concentration of the identified trigger substances in the selected foods, weight values associated with the identified trigger substances contained in the selected foods indicative of the relative correlation between the trigger substance and the occurrence of the selected health condition, and the selected risk factors.

16. The computer program product of claim 15, wherein the program instructions further comprise eighth program instructions for communicating data indicative of a summary report, comprising the selected health condition, the one or more identified foods, the calculated probability of causation of the selected health condition by the one or more identified foods, the identified trigger substances associated with the selected foods, and the identified risk factors to a user computing device.

17. The computer program product of claim 16, wherein the system is configured to calculate probabilities for a plurality of selected health conditions and to communicate a plurality of summary reports to the user computing device.

18. The computer program product of claim 15, wherein the second program instructions identifies trigger substances by cross referencing a trigger substances database with the selected health conditions, wherein the third program instructions identifies foods by cross referencing a foods database with the identified trigger substances, and wherein the fifth program instructions identifies risk factors by cross referencing a risk factors database with the selected health conditions.

19. The computer program product of claim 15, wherein the concentration of the trigger substance comprises one of an actual value and a relative value.

20. The computer program product of claim 15, wherein the program instructions further comprise ninth program instructions to modify the probabilities of causation of a health condition by a trigger food by adjusting weight values assigned to a trigger substance associated with the trigger food using one of a probabilistic method analysis and Bayesian analysis responsive to the first program instructions receiving data indicative of a plurality of selected health conditions caused by the same trigger substance.

* * * * *